United States Patent [19]

Houbiers et al.

[11] 4,169,839

[45] Oct. 2, 1979

[54] METHOD OF PREPARING A 3-IODOTHIOPHENE

[75] Inventors: Joannes P. M. Houbiers, Tegelen; Francina H. J. Thijssen, Venlo, both of Netherlands

[73] Assignee: Ocë-Andeno B.V., Venlo, Netherlands

[21] Appl. No.: 963,672

[22] Filed: Nov. 27, 1978

[30] Foreign Application Priority Data

Dec. 6, 1977 [GB] United Kingdom ............... 50749/77

[51] Int. Cl.$^2$ ........................................... C07D 333/12
[52] U.S. Cl. .................................................... 549/81
[58] Field of Search ....................................... 260/332.5

[56] References Cited

PUBLICATIONS

Wagner, "Synth. Org. Chem." (1965) pp. 93, 94.

Primary Examiner—A. Siegel
Attorney, Agent, or Firm—Albert C. Johnston

[57] ABSTRACT

A method for preparing a 3-iodothiophene from a corresponding 3-bromothiophene comprising reacting with copper(I)iodide in a polar aprotic solvent and at an elevated temperature a 3-bromothiophene of formula

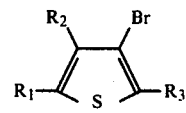

wherein
$R_1$ is H or a $C_{1-4}$ alkyl group,
$R_2$ is H or a $C_{1-2}$ alkyl group and
$R_3$ is H or a $C_{1-2}$ alkyl group,
with the proviso that not more than one of $R_2$ and $R_3$ is an alkyl group.

9 Claims, No Drawings

METHOD OF PREPARING A 3-IODOTHIOPHENE

This invention relates to a method for preparing a 3-iodothiophene compound from a corresponding 3-bromothiophene compound.

It is known that 3-bromothiophene can be converted into 3-iodothiophene. The preparation of 3-bromothiophene from 2, 3, 5-tribromothiophene is described by Gronowitz and Raznikiewicz in Organic Syntheses, Coll. Vol. V (1973), page 149. Conversion into 3-iodothiophene can be accomplished as described by Gronowitz in "Advances in Heterocyclic Chemistry", Vol. 1, pg. 42 (Academic Press, New York, 1963). According to that method 3-thienyllithium is prepared through halogen-metal interconversion between 3-bromothiophene and n-butyllithium at −70° C., at which temperature 3-thienyllithium is stable enough to be employed as the reagent for the preparation of 3-substituted thiophenes such as 3-iodothiophene.

The known method suffers from several drawbacks which make it hardly applicable on a plant scale, thus limiting it to laboratory scale use. One of these drawbacks, the very low reaction temperature, is self-evident. Another drawback is the need to use butyllithium which, apart from being expensive, necessitates a variety of special provisions, notably safety precautions, because it is quite a dangerous inflammable substance.

The object of the present invention is to provide a simple method for preparing 3-iodothiophene that obviates the drawbacks mentioned above.

Another object of the invention is to provide a method by which not only 3-iodothiophene but also various alkyl-substituted 3-iodothiophenes can be synthesized easily and with good yields.

It has been found that these objects can be met by a method in which, for preparing a 3-iodothiophene compound, a corresponding 3-bromothiophene is reacted with copper (I) iodide in a polar aprotic solvent and at an elevated temperature, the 3-bromothiophene being of the formula

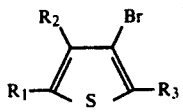

wherein
R$_1$ is H or a C$_{1-4}$ alkyl group,
R$_2$ is H or a C$_{1-2}$ alkyl group and
R$_3$ is H or a C$_{1-2}$ alkyl group,
with the proviso that not more than one of R$_2$ and R$_3$ is an alkyl group.

This method is particularly advantageous because of the relative ease of practicing it and of the relatively high yields that can be attained.

The method is highly suitable for the preparation of 3-iodothiophenes from 3-bromothiophenes of the formula

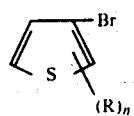

wherein n=0, 1 or 2 and R represents a C$_{1-2}$ alkyl group,
and especially for the preparation of 3-iodothiophene from 3-bromothiophene. In the former case the two positions ortho to the Br atom, of course, may not be occupied by an alkyl group simultaneously.

The reaction can be effected with the use of an amount of copper (I) iodide varying from a deficiency to an excess. The amount of copper (I) iodide lies in the range of 0.5 to 2.5 moles, and especially 1.2 to 1.7 moles, per mole of the 3-bromothiophene compound.

Any of various polar aprotic solvents may be used as the medium for carrying out the reaction. Examples of suitable polar aprotic solvents are dimethyl sulphoxide (DMSO), dimethylformamide (DMF), pyridines such as 2-, 3- and 4-picoline, isoquinoline and hexamethyl phosphoric acid triamide (HMPA). Preferably, quinoline is used because it is easily recuperated. Moreover, the highest yields are obtained in this solvent.

The reaction must be carried out at an elevated temperature. The temperature in general should be above 100° C., and preferably a temperature between 120° and 160° C. is employed.

The 3-iodothiophene compounds obtained by the method of the invention are useful as intermediates, e.g. in organic chemistry research, and for the preparation of a 3-thienylmalonic acid or ester thereof according to the disclosure of a copending U.S. patent application, Ser. No. 963,980 filed Nov. 24, 1978.

The following examples further illustrate the practice of the invention.

EXAMPLE 1

A mixture of 326 g (2.0 moles) of 3-bromothiophene and 571 g (3.0 moles) of copper (I) iodide in 750 ml quinoline was stirred during a period of 12 hours at a temperature of 140° C. After the reaction mixture had been cooled down to 70° C., 750 ml water and 750 ml concentrated HCl were added. The mixture was then steam distilled, and the distilled organic phase, after separation from the aqueous phase, was washed with a solution of bicarbonate, dried and fractionated under reduced pressure. An amount of 126 g 3-iodothiophene was collected, which corresponds to a yield of 30%. The first runnings (238 g having a boiling range of 66°–87° C. at 30 mm Hg) contained, apart from non-reacted 3-bromothiophene, another 63.0 g (=15%) of 3-iodothiophene.

EXAMPLE 2

A mixture of 97.8 g (0.6 moles) of 3-bromothiophene and 171.4 g (0.9 moles) of copper (I) iodide in 400 ml quinoline was stirred during a period of 20 hours at a temperature of 140° C. Then the heating and stirring was stopped. After the reaction mixture had been cooled down to 40° C., 600 ml water and 400 ml concentrated HCl were added. The precipitated copper salts were collected on a Buchner funnel by filtration, crushed in a mortar and washed with petroleum-ether 40–60 (five times with 100 ml each). The aqueous phase was extracted twice with 100 ml petroleum-ether 40–60. All organic phases were joined and dried over magnesium sulphate. After removal of the petroleum-ether under reduced pressure the result was only 90 g of a product still containing petroleum-ether.

The aqueous layer and the copper salts were put together and this mixture steam distilled in a Dean-Stark apparatus. This resulted in 25 g of an oily product which was combined with the afore-mentioned 90 g. Purification by distillation over a 99 cm vigreux column yielded:

(1) a fraction of 54.2 g having a boiling range of 90°–95° C. (120 mm Hg); $n_D^{20} = 1.5939$. GLC analysis showed this to consist of 97% 3-bromothiophene and 3% 3-iodothiophene.

(2) a fraction of 45.1 g having a boiling range of 100°–105° C. (65 mm Hg); $n_D^{20} = 1.6572$. GLC analysis showed this to consist of 1% 3-bromothiophene and 99% 3-iodothiophene.

(3) a residue of 6 g, containing according to GLC analysis another 3.6 g 3-iodothiophene.

The quantity of non-reacted 3-bromothiophene thus amounted to 53.1 g (0.326 moles) or 54.3% calculated to the starting amount of 3-bromothiophene. The total quantity of 3-iodothiophene amounted to 49.9 g (0.238 moles), corresponding to 39.7% calculated to the starting amount of 3-bromothiophene or 87% calculated to the consumed 3-bromothiophene.

EXAMPLE 3

This example illustrates variations of the yield of 3-iodothiophene which occurred with variations of the quantity of copper (I) iodide employed.

Mixtures of 65.2 g (0.4 moles) of 3-bromothiophene and varied amounts of copper (I) iodide were stirred during a period of 18 hours at a temperature of 140° C. in 250 ml quinoline. After the temperature had dropped to 70° C., 150 ml water and 250 ml concentrated HCl were added. Steam distillation resulted in an aqueous layer which was not analysed and an organic phase in which the quantities of 3-bromo- and 3-iodothiophene were determined by GLC analysis. The amounts of reactants employed and the results are set forth in Table I.

TABLE I
RESULTS
(the organic phase after the steam distillation)

| Starting Amounts | | weight of the organic phase in grams | 3-bromothiophene | | | 3-iodothiophene | | |
|---|---|---|---|---|---|---|---|---|
| moles 3-bromo-thiophene | moles CuI | | grams | moles | percentage | grams | moles | percentage* |
| 0.40 | 0.04 | 64.4 | 54.7 | 0.34 | 84 | 4.6 | 0.022 | 5.5 |
| 0.40 | 0.08 | 65.6 | 50.6 | 0.31 | 78 | 9.5 | 0.045 | 11.3 |
| 0.40 | 0.16 | 67.5 | 50.9 | 0.31 | 78 | 15.8 | 0.075 | 19 |
| 0.40 | 0.28 | 68.7 | 42.0 | 0.26 | 64 | 22.8 | 0.11 | 27 |
| 0.40 | 0.40 | 70.6 | 39.0 | 0.24 | 60 | 30.0 | 0.14 | 36 |
| 0.40 | 0.52 | 71.4 | 36.1 | 0.22 | 55 | 33.8 | 0.16 | 40 |
| 0.40 | 0.60 | 71.2 | 35.5 | 0.22 | 54 | 34.9 | 0.17 | 42 |

*percentages are calculated to the amount of 3-bromothiophene started from.

EXAMPLE 4

A mixture of 88.5 g (0.50 moles) of 3-bromo-4-methylthiophene and 143.3 g (0.75 moles) of copper (I) iodide in 188 ml quinoline was stirred during a period of 18 hours at a temperature of 140° C. After the reaction mixture had been cooled down to 70° C., 188 ml water and 188 ml concentrated HCl were added. The resultant mixture was then steam distilled. The aqueous phase of the distillate was extracted with chloroform. The chloroform phase was joined with the organic phase and then dried over magnesium sulphate. After removal of the solvent under reduced pressure the residue (92.7 g) was distilled at 10 mm Hg.

The first runnings being neglected, a 25 g fraction was obtained which consisted of 3-iodo-4-methylthiophene (90%) and 3-bromo-4-methylthiophene (10%).

EXAMPLE 5

A mixture of 16 g (0.084 moles) of 3-bromo-2, 5-dimethylthiophene and 34.3 g (0.18 moles) of copper (I) iodide in 60 ml quinoline was stirred during a period of 17 hours at a temperature of 140° C. Then the reaction mixture was cooled to 80° C. and 60 ml water and 60 ml concentrated HCl were added. The mixture was stream distilled in a Dean-Stark apparatus. The organic phase of the distillate was isolated and dried over magnesium sulphate. 21.5 g of a crude reaction product resulted which by GLC analysis contained 9.3 g 3-bromo-2,5-dimethylthiophene and 5.4 g (0.023 moles, or 27%) 3-iodo-2,5-dimethylthiophene. A 99% sample obtained by distillation showed a $n_D^{20} = 1.6108$.

EXAMPLE 6

A mixture of 43.8 g (0.2 moles) of 3-bromo-2,5-diethylthiophene and 57.1 g (0.3 moles) of copper (I) iodide in 100 ml quinoline was stirred during a period of 24 hours at a temperature of 140° C. and then poured out into a mixture of 175 g melting ice, 175 ml concentrated HCl and 175 ml chloroform. The chloroform layer was separated, washed with an aqueous solution of sodium bicarbonate and dried over magnesium sulphate. After removal of the solvent the residue was fractioned by spinning band distillation.

Apart from 49% unreacted 3-bromo-2,5-diethylthiophene, 25.6% of 3-iodo-2,5-diethylthiophene ($n_D^{20} = 1.5850$) was obtained. The yield calculated to the amount of consumed 3-bromo-2,5-diethylthiophene amounted to 50.2%.

While the foregoing examples illustrate the best mode presently ascertained for carrying out the invention, it is to be understood that the method described may be practised in other ways and that further experimentation for optimizing its results will lead to yields higher than those mentioned in the examples.

What is claimed is:

1. A method for preparing a 3-iodothiophene comprising reacting with copper(I)iodide in a polar aprotic solvent and at an elevated temperature a 3-bromothiophene of the formula

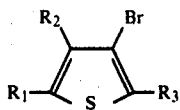

wherein
- $R_1$ is H or a $C_{1-4}$ alkyl group,
- $R_2$ is H or a $C_{1-2}$ alkyl group and
- $R_3$ is H or a $C_{1-2}$ alkyl group, with the proviso that not more than one of $R_2$ and $R_3$ is an alkyl group.

2. A method as claimed in claim 1 in which said 3-bromothiophene is one of the formula

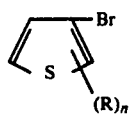

wherein n=0, 1 or 2 and R represents a $C_{1-2}$ alkyl group, with the proviso that not more than one position ortho to the Br atom carries an alkyl group.

3. A method as claimed in claim 2 in which n=0.

4. A method as claimed in claim 1, 2 or 3 in which the reaction is carried out by the use of 0.5 to 2.5 moles of copper (I) iodide per mole of said 3-bromothiophene.

5. A method as claimed in claim 1, 2 or 3 in which the reaction is carried out by the use of 1.2 to 1.7 moles of copper (I) iodide per mole of said 3-bromothiophene.

6. A method as claimed in claim 1, 2 or 3, said polar aprotic solvent being dimethyl sulphoxide, hexamethyl phosphoric acid triamide or quinoline.

7. A method as claimed in claim 1, 2 or 3, said polar aprotic solvent being quinoline.

8. A method as claimed in claim 1, 2 or 3 in which the reaction is carried out at a temperature between 120° and 160° C.

9. A method for preparing a 3-iodothiophene which comprises reacting with cuprous iodide in quinoline at a temperature between 120° and 160° C. with said iodide present in an amount of 1.2 and 1.7 moles per mole of 3-bromothiophene, a 3-bromothiophene selected from the group consisting of 3-bromothiophene, 3-bromo-2-methyl or 2-ethyl-thiophene, 3-bromo-4-methyl or 4-ethyl-thiophene, 3-bromo-2,5-dimethyl or 2,5-diethyl-thiophene, 3-bromo-4,5-dimethyl or 4,5-diethyl-thiophene and 3-bromo-5-methyl or 5-ethyl-thiophene.

* * * * *